United States Patent [19]

Jäckle

[11] Patent Number: 4,686,011
[45] Date of Patent: Aug. 11, 1987

[54] METHOD FOR THE PROTECTION OF AND/OR MONITORING OF CHANGES IN A REFERENCE SYSTEM IN ANALYTICAL MEASURING ENGINEERING, AND REFERENCE SYSTEM WITH A REFERENCE ELECTRODE

[75] Inventor: Heiner G. Jäckle, Stuttgart, Fed. Rep. of Germany

[73] Assignee: Conducta Gesellschaft fur Mess-und Regeltechnik mbH + Co., Gerlingen, Fed. Rep. of Germany

[21] Appl. No.: 717,340

[22] Filed: Mar. 29, 1985

[30] Foreign Application Priority Data

Mar. 30, 1984 [DE] Fed. Rep. of Germany ....... 3411799
Mar. 26, 1985 [DE] Fed. Rep. of Germany ....... 3510868

[51] Int. Cl.⁴ .................... G01N 27/30; G01N 27/46
[52] U.S. Cl. .................................... 204/1 T; 204/401; 204/406; 204/408; 204/412; 204/435; 324/425; 324/438
[58] Field of Search ............. 204/401, 412, 416, 435, 204/408, 1 T, 406; 324/425, 438

[56] References Cited

U.S. PATENT DOCUMENTS 4,461,998  7/1984  Kater .................................. 324/438
4,592,823  6/1986  Gregory ............................. 204/409

Primary Examiner—G. L. Kaplan
Attorney, Agent, or Firm—McAulay, Fields, Fisher, Goldstein & Nissen

[57] ABSTRACT

Method for the protection and/or monitoring of a reference system with reference electrode in analytical measuring techniques, and reference system therefor, wherein an additional monitor electrode is provided for self-monitoring the outer bridge electrolyte (16) for contamination, the additional monitor electrode being arranged to permit measuring of the pH value (pX value) of the bridge electrolyte which is adjusted to the same pH value (pX value) as the reference electrolyte. A fault signal is released when a potential difference occurs between the additional electrode and the real reference electrode of the reference system. Further, the bridge electrolyte is preferably connected with the measured solution in pressure-balancing relationship via a flexible diaphragm arranged in the wall of the vessel containing the bridge electrolyte which diaphragm may also be designed to serve as mounting for the said first diaphragm.

14 Claims, 3 Drawing Figures

METHOD FOR THE PROTECTION OF AND/OR MONITORING OF CHANGES IN A REFERENCE SYSTEM IN ANALYTICAL MEASURING ENGINEERING, AND REFERENCE SYSTEM WITH A REFERENCE ELECTRODE

BACKGROUND OF THE INVENTION

The present invention relates to a method and a reference system for monitoring changes in a fluid. Reference electrodes providing a constant reference potential, for example for pH or redox measurements, have been previously known also in the form of so-called electrolyte bridge systems comprising two diaphragms arranged in series (German Patent Publication No. 32 03 406, German Patent Publication No. 32 03 407). Such reference electrodes consist preferably of a silver/silver chloride electrode immersed in a solution of a constant chloride ion concentration. In the simplest of all cases this solution, which may also be gel-fixed, is connected with the measured solution via a diaphragm. It is, however, problematic in such reference systems that they are not constant as regards their potential because of the possibility of contamination from the outside which can never be excluded. Diffusion may occur through the diaphragm in both directions, due to concentration differences between the reference electrolyte and the measured solution, and when measured solution migrates into the interior of the reference electrode, there is a risk that the diaphragm may be obstructed due to crystallization and that the before-mentioned change, namely contamination of the reference electrolyte and the derivation system may occur. In the opposite direction, a loss of reference electrolyte or changes in concentration of the electrolyte due to so-called ablution may occur. In this connection and in supplementation of the generally accepted concept of diffusion, hydraulic movement of the medium through the diaphragm must be considered also in view of the required hydraulic permeability of the diaphragm or diaphragms, the before-mentioned movements being caused by pressure differences resulting from over or underpressure of the measured solution relative to the pressure of the reference electrolyte, or simply from variations in temperature entailing changes in the differential pressure. Another possibility consists in sealing the reference electrode off hermetically against the outside and filling its interior completely so that any external pressure variations of the measured solution cannot provoke hydraulic movement through the diaphragm. In this case, however, problems may be encountered as regards the necessary highly precise filling in which under certain circumstances air bubbles may be trapped so that no sufficiently high counterpressure can build up in the reference system to counteract the varying external pressure of the measured solution. Moreover, when the reference electrode is sealed off hermetically, hydraulic movement through the diaphragm may be obtained already as a result of temperature variations which in the case of repeated substantial temperature differences may lead to something like "breathing" of the enclosed volume, and this again results in hydraulic migration through the diaphragm in both directions, even in the hermetically sealed system.

Finally, it is a drawback of the known reference systems that the risk of contamination of the reference electrolyte and the derivation system can never be excluded completely, not even in systems providing optimum protection against diffusion, and that the user has no means to know whether or not and to what extent this is actually the case in the system operated by him and whether or not maintenance, exchange or adjustment is required.

Now, it is the object of the present invention to improve a reference system for use in analytical measuring techniques, that may already have been optimized as regards diffusion and pressure difference and which comprises two diaphragms arranged in series, so as to render it capable of indicating automatically its condition and insofar also any need for maintenance or exchange, and of providing further the facultative possibility to ensure that any exchange of fluid through the diaphragm, in particular under the aspect of hydraulic movement caused insofar by over or underpressure of the measured solution and/or by temperature changes, is practically excluded.

ADVANTAGES OF THE INVENTION

The monitoring method and/or the reference system of the invention offer the advantage that any error condition is indicated safely by an electric signal, for example for warning purposes or the like, already when a change has occurred in the bridge electrolyte and the pH measurement as such is still absolutely in order because the inner reference electrolyte has not been affected yet. Considering that the bridge electrolyte can be exchanged easily, the reference system according to the invention offers the possibility of correcting any faulty influences, variations in concentration of the bridge electrolyte and similar negative effects before they have reached or influenced the reference system as such.

For the purpose of clarifying the invention and the scope of the invention it is pointed out expressly that the terms pH measuring electrode or pH reference electrode, pH-sensitive electrode, or the like, which will be used almost exclusively hereafter, are meant to include also the general terms of potentiometric measuring electrode or reference electrode, which may also be described as pX electrode, wherein X is the chemical symbol of the ion to be measured. Accordingly, whenever the term pH electrode is used hereafter this is done regardless of the context for clarity's sake and in order to avoid constant repetitions and the need for constant references to the general term of potentiometric measuring electrode.

A particularly advantageous feature of the invention is to be seen in the arrangement of a pH reference (glass) electrode in the vessel or glass rod which contains the reference electrolyte exhibiting a constant pH value for the purpose of supplying the reference potential which in conjunction with the pH measuring electrode immersed in the solution to be measured or, to express it in a more general manner, in conjunction with the pX electrode permits measuring of the (hydrogen) ion concentration of the solution, and further in the additional combined arrangement of a pH-sensitive electrode in the vessel of the reference system in which case the latter pH electrode or pX electrode monitors the ion concentration of the bridge electrolyte present at any time. Considering that the measured solution can initially migrate into the bridge electrolyte only via the first, outer diaphragm, leaving the reference electrolyte completely unaffected at that time, it is possible to obtain information on a possible fault or change of the bridge electrolyte by differential measurements and comparison of the potential supplied by the bridge electrolyte which monitors the pH electrode with the reference potential. An alarm may be released when a pre-determined, preferably very low threshold value is exceeded.

The invention provides further the advantage that the flexible diaphragm—the term flexible diaphragm as used herein includes any type of compressible wall material capable of fulfilling the functions described further below—exhibits in the wall area between the transition or bridge electrolyte and the solution measured in any case a mobility sufficient to balance and compensate any compressible components or materials, for example in the form of one or more air bubbles, or volume changes caused by temperature variations and the resulting thermal expansions so that pressure differences are balanced without any external pressure compensation, which in turn excludes any internally directed hydraulic movement that would result in the feared contamination of the bridge electrolyte.

Another advantage of the present invention which eliminates in particular the problems resulting from the fact that the contaminable silver/silver chloride element tends to form chemical compounds leading to potential drifts, that the silver chloride tends to peel and that, in particular, there exists a detrimental interdependence with the chloride ion concentration which, although theoretically being held on a constant level by saturation actually does not exclude variations due to its temperature responsivity and the possibilities of over-saturation resulting therefrom, consists in that an intermediate or reference electrolyte of a constant, non-variable pH value is used in the manner of a buffer solution and that a pH glass electrode is immersed as reference electrode in this inner solution. Since the pH value of the reference electrolyte remains always constant, preferably in the rangeof pH 7, regardless of its degree of dilution and of the temperature variations to which it is subjected—the solutions used for this purpose may be conventional buffer solutions in the form of weak acids or bases with after-dissociation capabilities—the reference electrode will supply at all times a constant reference potential. The reference electrode immersed in the reference electrolyte of constant pH value is formed by a hermetically sealed and, thus, uncontaminable pH glass electrode.

According to an advantageous feature of a further embodiment of the invention, the arrangement of the reference derivation from AgAgCl is provided in a vessel containing a saturated KCl solution and immersed in turn in the vessel of the reference system which likewise contains a KCl intermediate electrolyte buffered at pH 7 and which also contains the monitoring electrode.

A particularly advantageous feature is seen in the arrangement of the first diaphragm within a pressure compensating diaphragm constituting the flexible diaphragm for compensating volume variations of the bridge electrolyte, and in the possibility to exchange the bridge electrolyte, i.e. the electrolyte providing the connection with the derivation system, early enough, related for example to pre-determined periods of time, to ensure that no contamination of the inner or reference electrolyte has been possible (yet) or has occurred if diffusion through the first diaphragm cannot be excluded due to differences in concentration.

BRIEF DESCRIPTION OF THE DRAWINGS

Certain embodiments of the invention are shown in the drawings and will be described hereafter in detail. In the drawings.

DESCRIPTION OF THE EXAMPLES OF THE INVENTION

The basic idea of the present invention consists in that in conjunction with the current code vessel or bridge electrolyte vessel, the current code electrolyte is connected with an inner electrolyte via a diaphragm, a pX electrode (pH glass electrode) is immersed additionally in the current code vessel or associated therewith for detecting by its sensitive element (glass diaphragm) the pH value (pX value) of the bridge electrolyte. The reference electrode immersed in the inner electrolyte of constant pH value (pH value) may be a pX electrode (pH glass electrode). Since the bridge electrolyte is also buffered at a pre-determined pH value or pX value which is preferably identical to the pH value (pX value) of the reference electrolyte or the inner electrolyte—otherwise the monitoring measurement would have to be related to a given threshold potential—both pH electrodes of the reference system must measure the same potential or, to say it in other words, the additional pH electrode is in a position to monitor the bridge electrolyte for possible contamination. The basic idea of the invention further comprises the feature to optimize the reference system comprising the electrolyte system with two diaphragms arranged in series in such a manner that the hydraulic movement which otherwise would have to be expected as a result of pressure variations to the measured solution and that in addition the monitor electrode immersed in the bridge electrolyte is provided preferably with a derivation system formed by a hermetically sealed and, thus, uncontaminable glass electrode. The second diaphragm is in this case arranged between the bridge electrolyte and the said monitor electrode.

Figure 1:
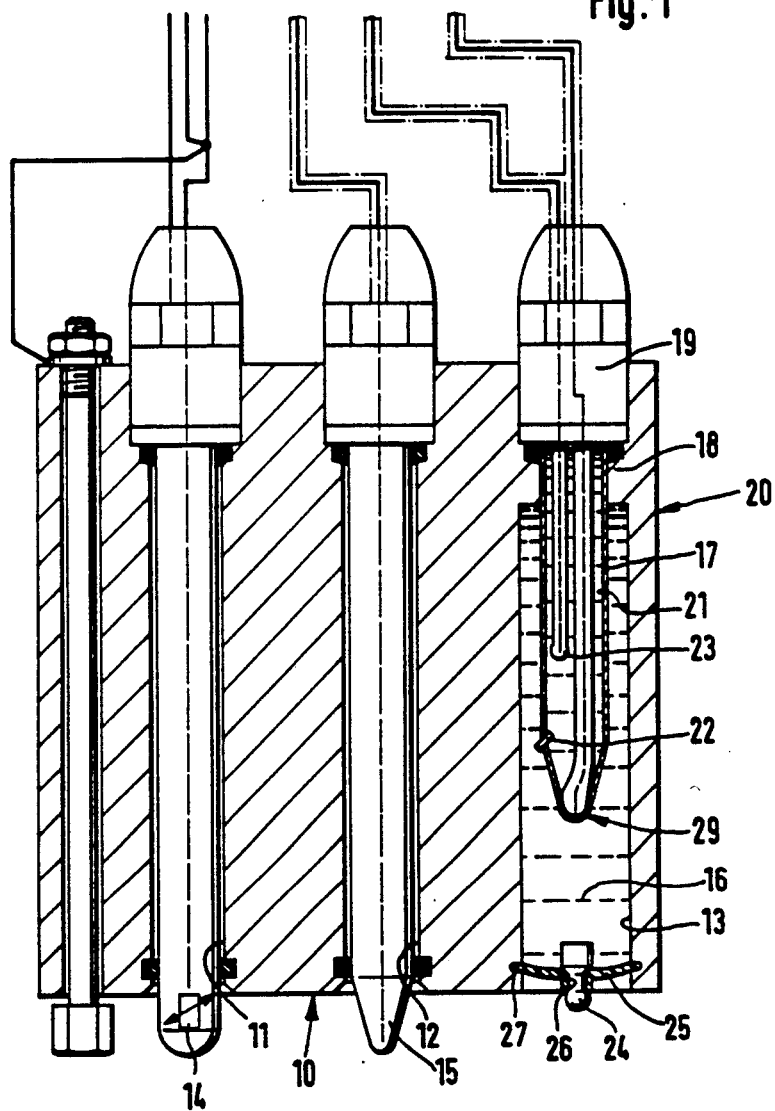
FIG. 1 shows a schematized section through a combination electrode system according to a first embodiment of the invention, in which a thermosensor, the actual pH electrode which is immersed in a solution to be measured, and the refence system incorporating certain features of the invention are mounted in a common block and thus united into a single package.

Referring now to FIG. 1 of the drawings, which shows a first embodiment of the invention, a mounting block which may consist of any desired material, such as metal, a plastic material, glass or the like, is designated by 10. It comprises three bores or receiving openings 11, 12, 13 for accommodating and seating, in the following order, a thermosensor 14, the pH electrode 15 immersed in the measured or process solution, and the reference system, the receiving opening 13 for the reference system forming at the same time by its inner wall the vessel which contains the bridge electrolyte 16 of the reference system. The reference electrode 19 is immersed in the said bridge electrolyte 16 though a neck portion of reduced cross-section with an intermediate seal 18. The reference electrode 19 consists preferably of a tube of a suitable material, in particular a glass which is highly fast to alkali, and which can be removed from the receiving opening 13 from above, for example for the purpose of exchanging the bridge electrolyte 16. The reference electrode 19 forms a current code vessel which may contain an inner electrolyte or reference electrolyte 21 of a constant pH value as buffer solution. The transition from the reference electrolyte 21 to the bridge electrolyte is formed by a second inner, smaller diaphragm 22 which may be disposed at any desired point and which in the embodiment shown is arranged at the side of the current code vessel.

A further essential inventive measure consists in that the reference derivation system taking the form of a hermetically sealed and, thus, uncontaminable pH glass electrode 23 is immersed in the reference electrolyte 21 of constant pH value which may preferably consist of a weak acid or base in the form of a buffer solution having the pH value 7 and retaining the latter even when diluted or subjected to other influences. Considering, therefore, that the pH value of the solution surrounding this second inner pH glass electrode of the reference system remains constant, the latter will always measure a constant reference potential. The reference electrolyte 21 of constant pH value is preferably gelled and exhibits insofar anti-contamination properties.

Another essential feature of the present invention is seen in that any hydraulic movements through the diaphragm caused by pressure variations between the process solution on the one hand and the bridge electrolyte which is connected with the said process solution via the first, comparatively larger diaphragm 24, are practically excluded because such pressure variations are eliminated by a special measure, i.e. at least one diaphragm-like wall portion which gives way to pressure exerted by the process solution.

In the embodiment shown, a flexible diaphragm is shown at 25 with an inner mounting 26 by which it is capable of seating simultaneously the first diaphragm. Accordingly, the diaphragm 25 is of annular shape due to its location and mounting 27, and has its outer circumference seated and clamped in a corresponding circumferential groove in the opening or bore 13 of the block 10. The diaphragm 25 consists of a suitable elastic material such as Teflon, Viton, or the like, for example a material as used for normal valve diaphragms, and is accordingly capable of balancing and compensating by its own movement, as will be easily understood, any volume changes occurring in the otherwise hermetically sealed total reference system due to influences of any type (compressible components, air bubbles, or the like in the bridge electrolyte, temperature-dependencies). Such a diaphragm which breathes under pressure differences makes it possible to do without any external pressure compensation so that substantially any contamination of the bridge electrolyte 16 which is anyway exchangeable and which also exhibits the pH value 7, is practically excluded at least as regards hydraulic migration due to over or underpressure of the measured solution.

Accordingly, it is an essential feature of the present invention that, as mentioned before, a pH-sensitive electrode 29 (pX-sensitive electrode) is arranged on the inside of the vessel 17 containing the reference electrolyte in such a manner that its (glass) diaphragm measures the pH value (pX value) of the bridge electrolyte 16. As mentioned before, the electrochemical series connection is then continued by the inner diaphragm 22, the inner reference electrolyte 21 with constant pH value as a buffer solution, and finally the pH glass electrode 23 supplying the reference potential for the measuring process as such.

The bridge space, i.e. the vessel holding the bridge electrolyte 16—formed in the present case by the bore 13 of the block 10—is filled with a bridge electrolyte having the same pH value as the reference electrolyte so that the two electrolytes 16 and 21 exhibit preferably the same pH value 7 and may also consist of the same buffer solution. This permits self-detection of any contamination of the bridge electrolyte 16 which due to remaining diffusion effects is (of course) the first element of the reference system to run the risk of contamination via the first diaphragm 24, in case anything should penetrate from the measured solution which acts to change the pH value and which of course will affect first of all the bridge electrolyte 16.

As such change or contamination of the bridge electrolyte occurs before any subsequent contamination of the reference electrolyte 21, which can never be excluded, a potential difference is obtained between the two pH glass electrodes 29 and 23 which would disappear only if the reference electrolyte were contaminated in the same manner. This difference which results from a Δ pH between the two electrolytes 16 and 21 is utilized for fault indication. The system may for example emit a suitable acoustic and/or optical signal, with the possibility to exchange the bridge electrolyte without any change to the remaining system, i.e. the reference electrode 19 and its pH glass electrodes.

In the embodiment shown in the drawing, the monitor pH glass electrode 29 is designed as an inner glass tube and guided upwardly, the glass tube being formed integrally with its glass diaphragm to form a sensitive element exposed in the vessel of the reference electrode 19 to the action of the bridge electrolyte 16.

Figure 2:
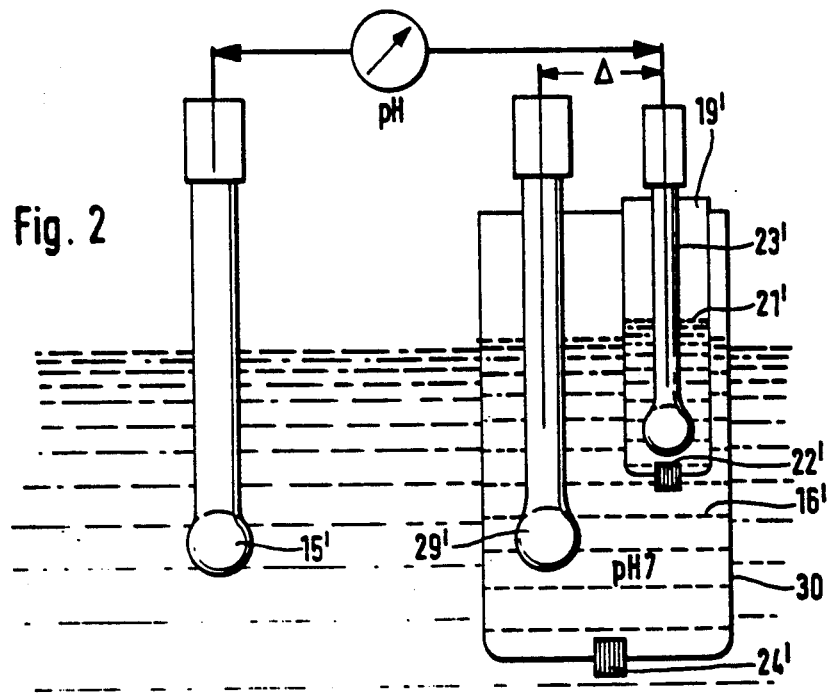
FIG. 2 shows a further embodiment of the invention in which the reference system electrode and the monitor electrode are immersed separately in the bridge electrolyte.

Another embodiment of the invention which differs from the embodiment of the monitor system for pH measurements just described only by a different structure, but which has the same basic function, is shown in FIG. 2.

This embodiment comprises likewise a first vessel 30 containing the bridge electrolyte 16' and immersed in the process solution whose varying pH value is to be determined; the inner reference electrode 19' forming the inner electrolyte or reference electrolyte 21' and exhibiting at 22' a transition to the bridge electrolyte 16' formed by an inner diaphragm is immersed in the said vessel 30. The uncontaminable pH electrode 23' (glass electrode) supplying the constant reference potential for the pH measurement is immersed in the inner electrolyte 21', as known from conventional reference systems. The outer transition between the bridge electrolyte 16' and the measured solution is formed by an outer diaphragm 24'.

In the case of this reference system with simultaneous monitoring of the bridge electrolyte 16', a pH-sensitive monitor glass electrode 29' is immersed separately in the said bridge electrolyte 16', subject to the before-described condition that when the bridge electrolyte 16' is in perfect condition (for example pH 7 buffered) no Δ potential is encountered between the reference electrode 19' and the monitor electrode 29'. The pH-sensitive glass measuring electrode is shown at 15' and immersed in the usual manner directly in the measured solution. In this embodiment, all electrodes of the measuring chain and the reference monitoring chain are formed by chemically inert glass electrodes with glass diaphragms producing stable potentials, however with high-ohmic transitions so that even amplifiers or impedance transformers having very high input resistances can be employed for the measurement.

Figure 3:
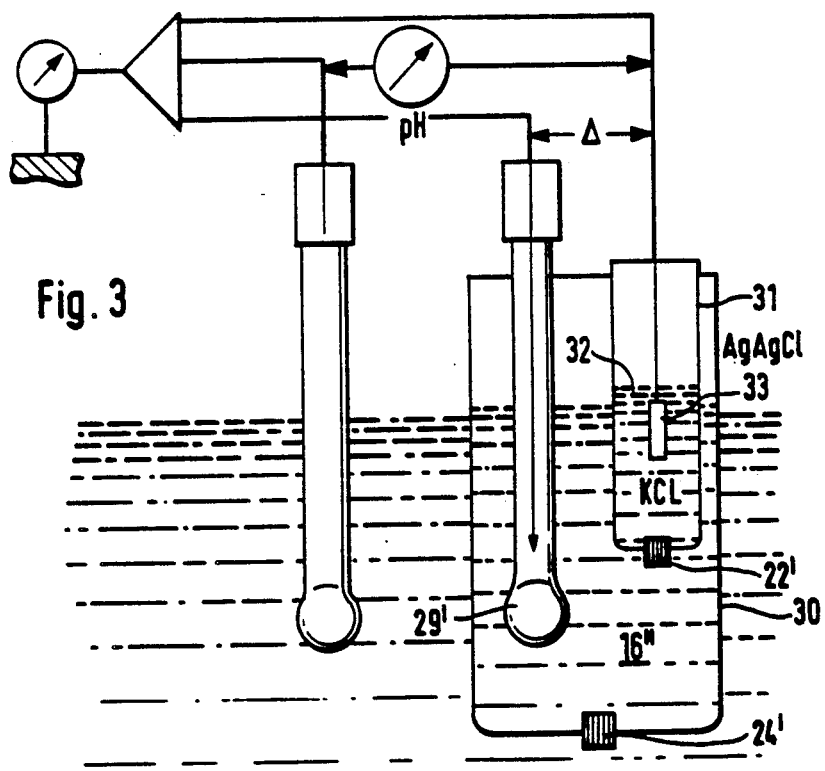
FIG. 3 shows an at least partially low-ohmic reference system with an AgAgCl derivation in a saturated KCl solution.

Another preferred embodiment of the invention which eliminates some of the technical problems, including that of the high impedance of the pH-sensitive glass electrodes used as reference electrode, is shown in FIG. 3. It comprises a vessel or chamber 31 immersed in the vessel 30' containing the bridge electrolyte 16'', which vessel 31 contains a liquid or solution 32 which has the anion in common with the salt of the derivation 33 immersed in the said liquid.

Accordingly, in practical use this constant-potential reference system follows the known electro-chemical definition that a metal, here preferably and usually silver, covered by a water-insoluble salt of the same metal (silver chloride), when immersed in a liquid which has the anion in common with the salt and which is of stable concentration relative to the anion, supplies a constant potential. Accordingly, the vessel 31 is filled in a preferred embodiment of the invention with a saturated potassium chloride solution (KCl) whereby the constant reference potential is ensured.

The intermediate electrolyte or bridge electrolyte consists preferably also of a pH 7 buffered potassium chloride solution, with the monitor electrode 29' which exhibits the same construction as in the embodiment shown in FIG. 2 immersed therein.

Such a pH measuring chain and monitor measuring chain arrangement offers the advantage that due to the AgAgCl derivation immersed in the saturated potassium chloride solution a low impedance can be achieved at least on one side in both measurements (pH measurement (pX measurement) and monitoring measurement). In spite of the low-ohmic generation of measuring and monitoring signals, further processing thereof is preferably high-ohmic, which means that they are supplied, for example, to operational or comparator amplifiers or impedance transformers with high-ohmic inputs so that the measuring results can be kept completely free from potential shifts which may for example occur due to resistance variations of the diaphragms 22', 24', for example when the latter get obstructed, and this also during the measuring phase, which in the case of low-ohmic signal generation could otherwise lead to drifting of the measuring signals, as shown in FIG. 3.

If the signal is generated in this manner, no additional potential compensation electrode, as employed under certain circumstances in the embodiments discussed before, will be required.

All features described in the following claims and shown in the drawing may be essential to the invention either individually or in any desired combination thereof.

I claim:

1. In a method for measuring ion concentrations and activities in a measured fluid with potentiometric measuring electrode for producing constant reference voltages comprising an electrolyte bridge system having a reference electrolyte and a bridge electrolyte with first and second diaphragms arranged in series with the bridge electrolyte therebetween, the improvement comprising monitoring changes in a reference system leading to potential drifts by the steps of detecting the occurrence of a potential difference resulting from a difference in pX value between the reference electrolyte and the bridge electrolyte and producing a fault signal when such difference occurs.

2. The method according to claim 1, further comprising hermetically sealing the connection between the bridge electrolyte and the measured solution and preventing building-up of pressure differences between the two electrolytes by providing at least certain flexible portions in the walls enclosing the bridge electrolyte.

3. The method according to claim 2, wherein the flexible wall portion is formed by a third diaphragm in which the first diaphragm is seated and which prevents hydraulic movements of the latter due to its mobility.

4. The method according to claim 1, wherein the system includes a reference electrode and a monitor electrode associated with said second diaphragm, the difference in potential being detected by comparing the potential generated by the reference electrode and a potential generated by the monitor electrode whose diaphragm measures the pX value of the bridge electrolyte.

5. In a system for measuring ion concentrations and activities in a measured solution with a reference system including a reference electrode and a reference electrolyte and a potentiometric measuring pX electrode comprising a vessel having a first bridge electrolyte connected with a measured solution via a first diaphragm, said reference electrolyte comprising a second inner electrolyte which is connected with the first bridge electrolyte via a second diaphragm, the improvement comprising: means for monitoring changes in the reference system leading to potential drifts comprising an additional monitor electrode for measuring the pX value of the first bridge electrolyte and wherein the first bridge electrolyte has the same pX value as the reference electrolyte.

6. The system according to claim 5, further comprising a hermetically sealed vessel containing the first bridge electrolyte disposed adjacent to the measured solution and having a wall portion comprising a flexible diaphragm for preventing building-up of a pressure difference between the measured solution and the first bridge electrolyte so that hydraulic movements through the first diaphragm are excluded.

7. The system according to claim 6, wherein the reference electrolyte is a buffer solution having the pH value 7 and the capability of after-dissociation.

8. The system according to claim 6, wherein the first diaphragm is disposed in and carried by the flexible diaphragm which comprises a flexible annular diaphragm between the measured solution and the bridge elctrolyte.

9. The system according to claim 5, wherein the additional monitor electrode comprises a pH glass electrode for monitoring the first bridge electrolyte including a glass tube in the vessel containing the reference electrolyte and having a sensitive element formed at its bottom integrally with the reference electrode wall and immersed in the bridge electrolyte.

10. The system according to claim 5, wherein the reference electrolyte is an electrolyte of constant pH value so that diffusion due to differences in concentration is prevented.

11. The system according to claim 10, wherein the first bridge electrolyte is pH 7 buffered.

12. The system according to claim 5, wherein the reference electrode is immersed in buffered reference electrolyte solution and comprises a hermetically sealed, uncontaminable pH glass electrode and the second diaphragm is arranged between said reference electrode and the bridge electrolyte.

13. In a system for measuring ion concentrations and activities in a measured solution with a reference system including a reference electrode and reference electrolyte, a potentiometric measuring pX electrode comprising a first bridge electrolyte which is connected with the measured solution by a first diaphragm and a second inner electrolyte which is connected with the first electrolyte by a second diaphragm, the improvement comprising: means for monitoring changes in the reference system leading to potential drifts comprising an additional monitor pX electrode for measuring the pX value of the bridge electrolyte and wherein the reference system which supplies a reference potential being formed by a metal/metal salt derivation immersed in a vessel containing a fluid which has the anion in common with the salt of the derivation and which is constant in concentration relative to the latter so that low impedance is obtained in the detection of measured values and monitoring values in the area of this part of the system.

14. The system according to claim 13 including a processing device having differential amplifiers with high input resistances, and leads connecting said measuring system with said processing device whereby all measured and monitoring signal values are supplied to said processing system.

* * * * *